United States Patent [19]

Suval

[11] Patent Number: 5,758,665
[45] Date of Patent: Jun. 2, 1998

[54] METHOD FOR TREATING VARICOSE VEINS

[76] Inventor: William D. Suval, 16003 Tuscola Rd. #F, Apple Valley, Calif. 92307

[21] Appl. No.: 749,970

[22] Filed: Nov. 14, 1996

[51] Int. Cl.⁶ .................................................. A61B 00/19
[52] U.S. Cl. ........................................................ 128/898
[58] Field of Search ............................ 128/898; 606/159, 606/167, 211, 225, 222, 148, 187; 600/217, 235

[56] References Cited

U.S. PATENT DOCUMENTS

| | | |
|---|---|---|
| Re. 28,932 | 8/1976 | Noiles et al. |
| 3,643,851 | 2/1972 | Green et al. |
| 3,717,294 | 2/1973 | Green |
| 3,954,108 | 5/1976 | Davis |
| 4,058,126 | 11/1977 | Leveen |
| 4,127,227 | 11/1978 | Green |
| 4,204,623 | 5/1980 | Green |
| 4,221,212 | 9/1980 | Miller ................................ 606/187 |
| 4,372,302 | 2/1983 | Akerlund ......................... 606/148 X |
| 4,517,965 | 5/1985 | Ellison ............................... 600/204 |
| 4,583,540 | 4/1986 | Malmin ............................ 606/148 X |
| 4,760,846 | 8/1988 | Mers Kelly et al. |
| 4,827,929 | 5/1989 | Hodge |
| 4,874,375 | 10/1989 | Ellison .............................. 604/164 |
| 4,877,028 | 10/1989 | Sandhaus |
| 4,881,939 | 11/1989 | Newman |
| 5,015,250 | 5/1991 | Foster .............................. 606/148 X |
| 5,035,701 | 7/1991 | Kabbara ............................... 606/148 |
| 5,254,095 | 10/1993 | Harvey |
| 5,282,812 | 2/1994 | Suarez, Jr. |
| 5,304,183 | 4/1994 | Gourlay et al. |
| 5,306,283 | 4/1994 | Conners |
| 5,312,422 | 5/1994 | Trott .................................... 606/148 |
| 5,366,458 | 11/1994 | Korthoff et al. |
| 5,611,357 | 3/1997 | Suval .................................. 128/898 |
| 5,611,358 | 3/1997 | Suval .................................. 128/898 |

FOREIGN PATENT DOCUMENTS 3525917  2/1986  Germany ........................... 606/167

OTHER PUBLICATIONS

Treatment of Long Saphenous Varicosities and Their Recurrence: A Long-Term Follow-Up, by Eric P. Lofgren, Surgey Of The Veins, Grune & Stratton, 1985, pp. 285-299.

A New Approach to Short Saphenous Vein Varicosities, by John T. Hobbs, Surgery Of The Veins, Grune & Stratton, 1985, pp. 301-321.

Varicose Veins, by Aksel G. Nordestgaard and Russell A. Williams, Vascular Surgery Principles And Practice, McGraw-Hill, 1994, 1987, pp. 841-851.

Primary Examiner—Vincent Millin
Assistant Examiner—Kelly O'Hara
Attorney, Agent, or Firm—Graham & James LLP

[57] ABSTRACT

A surgical method including the steps of forming an incision through a skin layer adjacent to a varicose vein with a single surgical device, and engaging the varicose vein with the single surgical device to permit removal of a selected portion thereof through the incision. The selected portion of the varicose vein is ligated subsequent to removal through the incision.

12 Claims, 4 Drawing Sheets

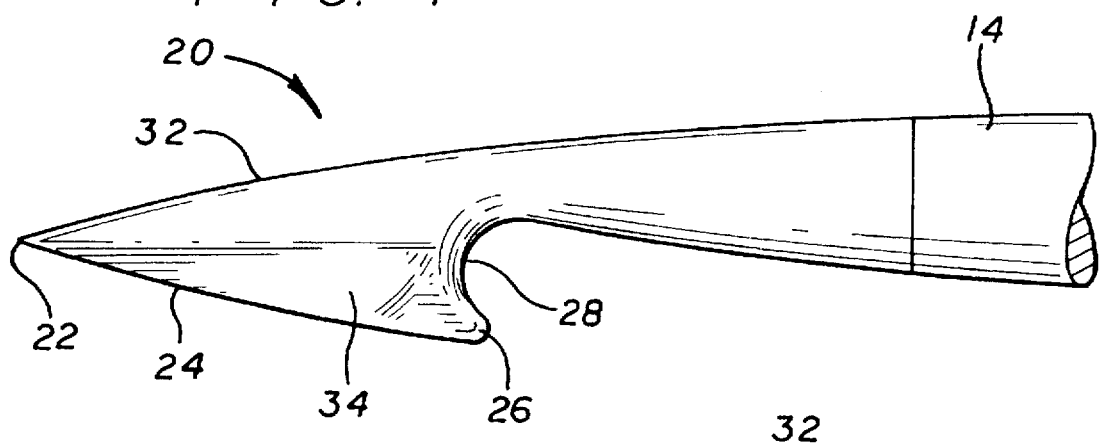
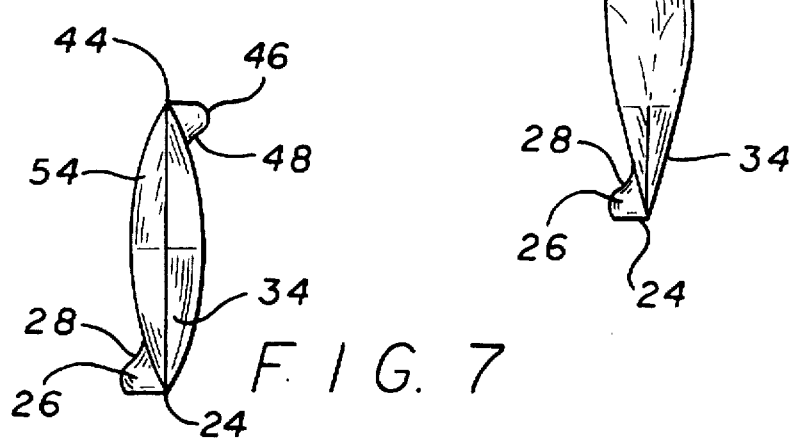
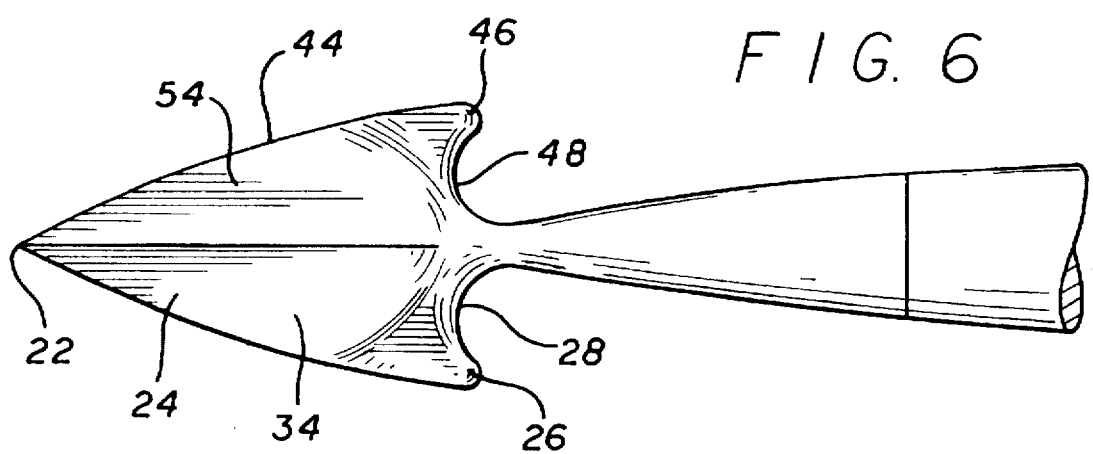

METHOD FOR TREATING VARICOSE VEINS

RELATED APPLICATION

This application relates to co-pending application Ser. Nos. 08/749,969, filed Nov. 14, 1996, for APPARATUS FOR TREATING VARICOSE VEINS and 08/747,805, filed Nov. 14, 1996, for APPARATUS FOR TREATING VARICOSE VEINS.

BACKGROUND OF THE INVENTION

1. Field of the Invention

The present invention relates generally to medical treatment, and more particularly, to a surgical method for treating varicose veins.

2. Description of Related Art

Varicose veins is a medical condition present in up to twenty-five percent of the adult population, and is especially prevalent among middle-aged women. The term "varicose" is derived from the Greek word for "grape-like" and refers to the torturous appearance of the afflicted veins. Patients suffering from varicose veins often experience various symptoms, including aching, itching, heaviness, swelling or cramping of the legs, while more serious complications of varicose veins can include thrombophlebitis, dermatitis, hemorrhage and ulcers. Even absent such complications, many patients seek medical treatment of varicose veins for primarily cosmetic reasons due to the generally unsightly appearance that characterizes the condition.

Specifically, varicose veins are a condition of the superficial veins of the legs in which the veins have become abnormally twisted, lengthened, or dilated. The condition is usually caused by inefficient or defective one-way valves within the veins. These one-way valves provide an important function in controlling blood pressure within the venous system of the legs. During walking, the leg muscles provide a musculovenous pump that compresses the veins and propels blood to the heart. Efficiency of the musculovenous pump is enhanced by the one-way valves within the veins that protect the venous system at the lower extremities from excess pressure generated by coughing, straining, lifting, standing or other such exertion. The superficial veins normally carry only ten to fifteen percent of the blood, with the remainder carried by the deep veins; however, the percentage of blood carried by the superficial veins can exceed these normal levels due to dilation of the superficial veins or thrombosis of the deep veins. As a result, the one-way valves can become incompetent which further increases retrograde pressure within the superficial veins. Since the superficial veins lie close to the skin layer and are poorly supported by the subcutaneous tissue, the increased retrograde pressure causes the varicose veins to be formed.

There are two known types of treatment for varicose veins. A first type of treatment comprises surgical removal of the superficial varicose veins, also referred to as "vein stripping." In the stripping technique, a surgeon first makes an incision at the groin area through which the saphenous vein is separated from the femoral vein. The saphenous vein is also dissected at the foot, and at that point, a vein stripper, such as a wire, is inserted into the lumen of the saphenous vein. The wire is then threaded through the saphenous vein to the incision at the groin. The wire includes a nut at an end thereof that catches on the foot end of the saphenous vein. The surgeon then removes the wire though the groin incision to gently extract the vein. It is further necessary to make multiple small incisions along the leg in order to disconnect the numerous tributary veins from the saphenous vein and to ligate these tributary veins. A phlebectomy hook may be used to capture a portion of the saphenous vein or tributary veins in order to extract it through one of the small incisions for ligation and/or removal of the vein portion. Once the saphenous vein is completely removed from the leg, the various incision wounds can be sutured closed.

The stripping technique represents a permanent solution in that the varicose vein condition cannot recur once the vein has been removed. Nevertheless, the technique has numerous significant drawbacks that render it an unsatisfactory treatment. The numerous incisions often leave substantial unsightly scars along the legs that can be as unpleasant in appearance as the original varicose vein condition. Moreover, the procedure is generally performed under general anesthesia and often requires an overnight hospital stay. There are also associated complications of the technique, such as blood loss, pain, infection, hematoma, nerve injury and swelling. After undergoing the stripping technique, a patient generally requires several weeks to recover. In view of these significant drawbacks, the stripping technique is recommended only for extreme cases of varicose veins, and for patients that are in sufficiently good health to handle the surgery.

A second technique for treating varicose veins is known as sclerotherapy. This technique involves injection of toxic fluids, such as sodium tetradecyl sulfate, into the veins to cause subsequent inflammation and sclerosis of the veins. The sclerosis results in localized scarring or closure of the veins, which forces rerouting of the blood away from the affected veins. The sclerotherapy technique is often combined with an operative procedure, such as ligation of a portion of the saphenous vein.

While the sclerotherapy technique is less surgically intensive than the stripping technique, it often does not represent a permanent or complete solution since it has a high rate of recurrence and cannot be applied to the saphenous vein in the upper thigh region due to the risk of sclerosis of the deep veins. Sclerotherapy has other potentially serious complications, including skin staining, ulceration, phlebitis, allergic or anaphylactic overdose, ischemia, skin or fat necrosis, and peripheral neuropathy. Notwithstanding these complications, patients must often undergo multiple courses of sclerotherapy treatment in order to completely alleviate the varicose veins to a satisfactory degree.

In view of these significant drawbacks, a critical need exists for a surgical method that reduces the invasiveness and associated recovery time of the conventional treatment for varicose veins.

SUMMARY OF THE INVENTION

The present invention satisfies the need for an effective surgical method for treating varicose veins. The surgical method comprises the steps of forming an incision through a skin layer adjacent to a varicose vein with a single surgical device, and engaging the varicose vein with the single surgical device to permit removal of a selected portion thereof through the incision. Thereafter, the selected portion of the varicose vein is ligated subsequent to removal through the incision.

In a first embodiment, the surgical device further comprises an elongated shaft having a scalpel edge that extends to an endpoint of a distal end of the elongated shaft and a hook provided at an end of the scalpel edge opposite from the endpoint. According to this first embodiment, the incision forming step further comprises pushing the endpoint of the scalpel edge through the skin layer, and the engaging step further comprises engaging the varicose vein with the hook.

In a second embodiment, the surgical device further comprises a needle extending from an end of an elongated shaft and having a sharpened tip. The surgical device further comprises a cylindrical sleeve concentrically disposed around the shaft and being adapted to move in sliding engagement with the shaft along an axial extent thereof. The needle and the cylindrical sleeve further have respective facing surfaces that define a gripping region therebetween. According to this second embodiment, the incision forming step further comprises pushing the sharpened tip through the skin layer, and the engaging step further comprises selectively moving the cylindrical sleeve relative to the shaft to vary a length of the gripping region.

A more complete understanding of the method for treating varicose veins will be afforded to those skilled in the art, as well as a realization of additional advantages and objects thereof, by a consideration of the following detailed description of the preferred embodiment. Reference will be made to the appended sheets of drawings which will first be described briefly.

BRIEF DESCRIPTION OF THE DRAWINGS

FIG. 4 is an enlarged side view of the surgical apparatus;

FIG. 5 is an end view of the surgical apparatus as viewed from a distal end thereof;

FIG. 6 is an enlarged side view of an alternative embodiment of the surgical apparatus;

FIG. 7 is an end view of the alternative embodiment of the surgical apparatus as viewed from a distal end thereof;

DETAILED DESCRIPTION OF THE PREFERRED EMBODIMENT

The present invention satisfies the need for a surgical method that would reduce the invasiveness and associated recovery time of the conventional treatment for varicose veins. In the detailed description that follows, like element numerals are used to describe like elements illustrated in one or more of the figures.

Figure 1:
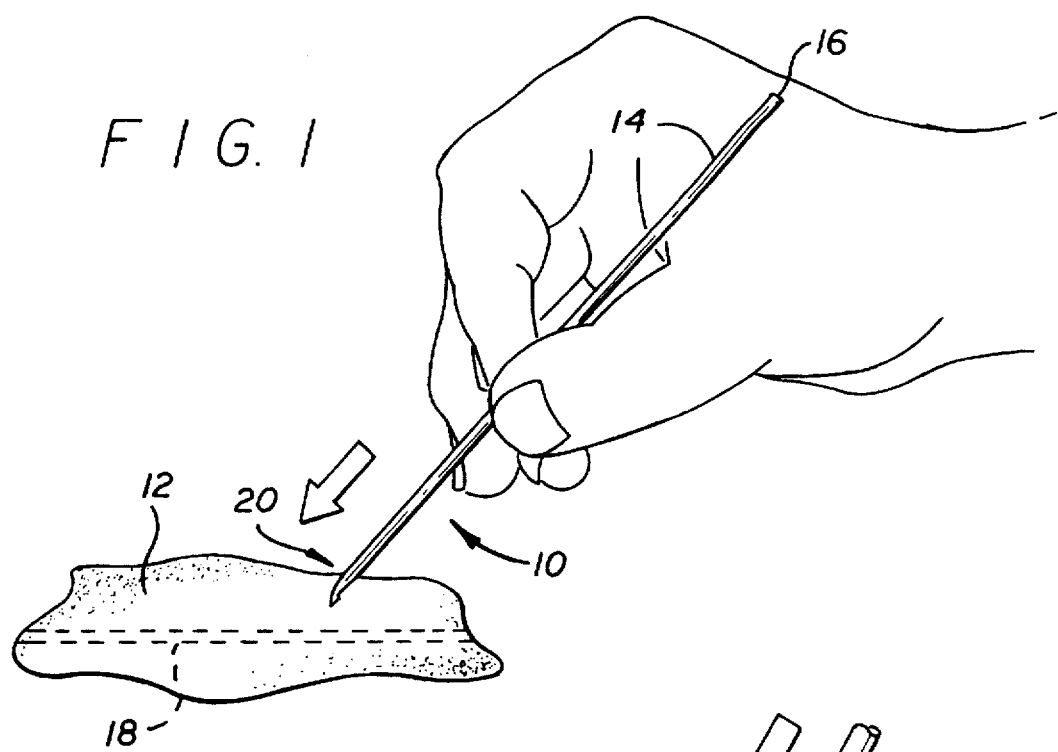
FIG. 1 is a perspective view of a surgeon using the surgical apparatus of the present invention.

Referring first to FIG. 1, a partial perspective view of a portion of the leg showing the skin layer 12, and a segment of a superficial vein 18 is illustrated. The superficial vein 18 lies between layers of subcutaneous tissue and sartorius muscle. The specific segment of superficial vein 18 requiring treatment may comprise the saphenous vein or one of its tributary veins, depending on the specific condition of the particular patient. Prior to treating the specific vein segment, the saphenous vein may be disconnected from the femoral vein, as known in the art.

In accordance with the present application, a single apparatus is used to form an incision through the skin layer 12 and engage the superficial vein 18 for extraction of the vein through the incision. Once extracted, the superficial vein segment may be ligated using known surgical techniques. Subsequently, the incision through the skin layer 12 heals normally, and by keeping the size of the incision relatively small, any scarring of the skin will be minimized. Moreover, the procedure can be performed on an out-patient basis without any of the usual complications of conventional surgical procedures.

As shown in FIGS. 4 and 5, a surgical apparatus 10 comprises an elongated shaft 14 having a gripping portion at a proximal end 16 thereof and a surgical portion 20 at a distal end. The shaft 14 is substantially cylindrical in shape, and may be comprised of a high strength material such as surgical-grade steel. The surgical portion 20 further comprises a scalpel 34 having an edge 24 that extends to an endpoint 22 of the distal end. At the opposite side of the distal end from the scalpel edge 24, the surgical portion 20 has a rounded or blunt surface 32. It should be appreciated that the scalpel edge 24 and endpoint 22 are intended to be sufficiently sharp so as to be used for performing surgical procedures. The surgical portion 20 may be removably attached to the shaft 14, such as by a threaded attachment, to promote disposal or sterilization of the surgical portion. The maximum width of the surgical portion 20 as measured in a direction perpendicular to a central axis of the shaft 14 may be approximately four millimeters, and in a preferred embodiment of the invention, the surgical portion may be available in several widths, including one, two, three and four millimeter sizes.

A hook 28 is provided that extends from a barb 26 which coincides with an end of the scalpel edge 24 opposite from the endpoint 22. The hook 28 is generally rounded, and the barb 26 provides a blunt end to the hook. The barb 26 may also be skewed so that it extends at an angle with respect to an axial direction of the shaft 14. The generally uniform diameter of the shaft 14 tapers slightly inwardly at the hook 28. As illustrated at FIGS. 6 and 7, the surgical portion 20 may also be provided with a pair of scalpels 34, 54 having respective edges 24, 44 that are disposed 180° apart from each other around the circumference of the shaft 14. Each of the respective scalpels 34, 54 have corresponding barbs 26, 46 and hooks 28, 48. The barbs 26, 46 may also be skewed so that they extend at opposite angles with respect to an axial direction of the shaft 14.

Figure 2:
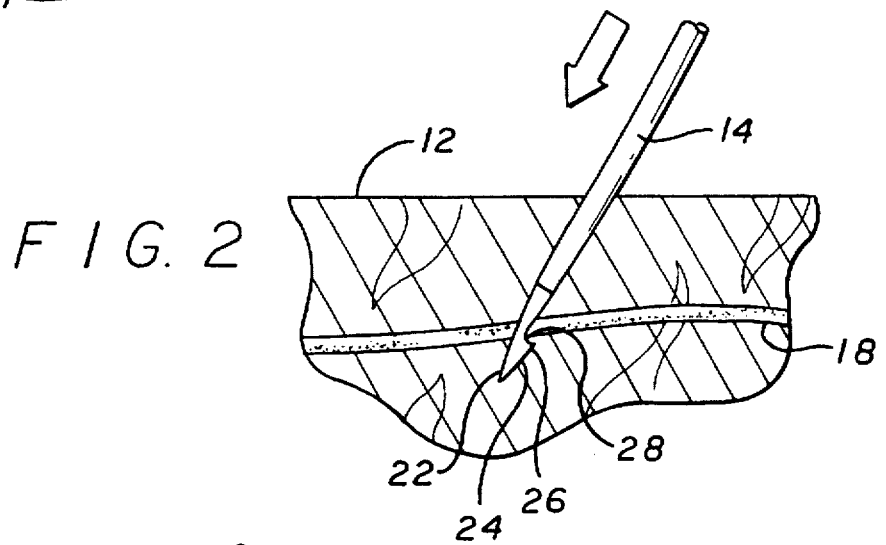
FIG. 2 is a partial perspective view of the surgical apparatus in engagement with an exemplary vein.
Figure 3:
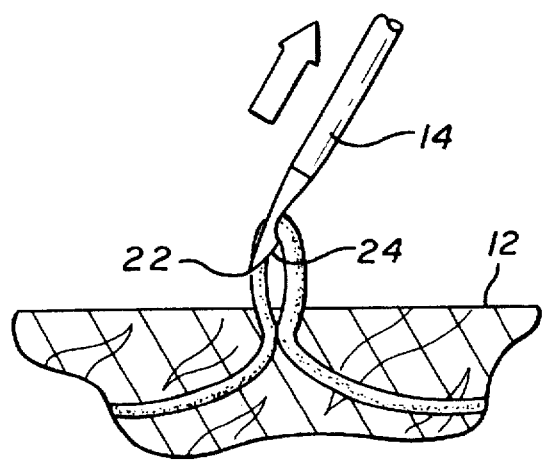
FIG. 3 is a partial perspective view of the surgical apparatus extracting a portion of the exemplary vein.

The use of the surgical apparatus 10 in performing a varicose vein surgical procedure is now described with reference to FIGS. 1 through 3. Prior to conducting the vein surgery, a surgeon traces a varicose vein segment with a marker on the skin surface while the patient is standing in an upright position. It should be appreciated that once the patient lies down, the blood pressure in the superficial saphenous veins will drop, causing the veins to collapse and be difficult to locate. Therefore, it is necessary to mark the veins prior to performing the surgery.

After selecting an appropriate segment of the varicose vein for removal and ligation, the surgical apparatus 10 is used to form an incision through the skin layer at the marked locations. Particularly, the incision may be formed by pushing the surgical portion 20 directly into the skin layer 12, which cuts easily due to the extreme sharpness of the endpoint 22 and scalpel edge 24. The surgical portion 20 is extended downward into the skin layer 12 until the barb 26 at the end of the scalpel edge 24 is slightly below the level of the vein 18. Then, the shaft 14 may be rotated slightly to cause the barb 26 to catch under the vein 18.

Thereafter, the surgical portion 20 is withdrawn from the skin layer 12 along the same axial direction that it was inserted. In so doing, the vein 18 will seat against the hook 28 and be withdrawn along with the surgical portion 20. It should be appreciated that the slight skewing of the barb 26 will better facilitate engagement between the hook 28 and the vein 18. By continuing to withdraw the surgical portion 20, the vein 18 will eventually be pulled outwardly through the incision formed through the skin layer 12. Once the vein 18 is exposed, the surgeon may remove the varicose vein segment and ligate the exposed ends of the vein following removal. Thereafter, the ligated portions of the vein 18 will return back-through the incision due in part to the elastic nature of the vein. The incision may then be closed using conventional techniques, such as by using tape strips.

By using a single surgical instrument having both a scalpel edge and a hook, the vein surgeon can perform the steps of forming the incision, grasping the vein, and withdrawing the vein in a single fluid motion. Under conventional surgical methods, the surgeon first makes an incision using a scalpel, then switches to a separate device having a hook to capture and withdraw the vein. Such conventional methods also tended to require a larger incision than that required by the present device, since the incision needed to be held open while the hook was inserted. Accordingly, the present apparatus and method permits the overall surgery time to be reduced, with associated benefits to the patient in terms of reduced recovery time and medical cost savings.

Referring now to FIGS. 8 through 13, an alternative embodiment of a surgical apparatus 60 is illustrated. As best illustrated in cross-section at FIG. 11, the surgical apparatus 60 comprises a gun-shaped device having an outer barrel 62, a handle 64, and a trigger 66. The handle 64 may be shaped to conform with the palm of a surgeon's hand to facilitate ease of use. The trigger 66 is integrally formed with the outer barrel 62 so that the two elements move together in unison relative to the handle 64. Similarly, the handle 64 is integrally formed with an inner barrel 84, and the inner barrel and outer barrel 62 comprise concentric cylinders that are slidably movable in an axial direction relative to each other. A portion of the inner barrel 84 extends outwardly of the outer barrel 62 in the distal direction. The inner barrel 84, outer barrel 62, handle 64 and trigger 66 may be formed of a rigid and lightweight material, such as thermoplastic.

At a distal end of the outer barrel 62, a limit pin 93 is provided which extends radially through the inner barrel 84. A pair of axial slots 95, 97 are disposed in parallel to each other on opposite sides of the inner barrel 84, so that the limit pin 93 extends through the respective slots. As a result, the maximum extent of axial movement of the outer barrel 62 and the inner barrel 84 is limited by interference between the limit pin 93 and the respective ends of the axial slots 95, 97. The limit pin 93 also passes radially through a tie rod 94 that provides a structural base for movement of a vein gripping portion of the apparatus 60, which will be further described below. The tie rod 94 is cylindrical in shape, having a diameter less than an inside diameter of the inner barrel 84 and is contained entirely within the inner barrel.

The tie rod 94 may be comprised of a high strength material, such as metal. A spring 86 is disposed within the inner barrel 84 having a first end pressed against a ledge 88 provided at an interior portion of the inner barrel and a second end pressed against an end portion 92 of the tie rod 94. The spring 86 maintains the inner barrel 84 biased in a position relative to the outer barrel 62 such that the limit pin 93 is held against a distal end of the axial slots 95, 97. By applying a squeezing pressure between the handle 64 and the trigger 66, the inner barrel 84 moves axially in the distal direction relative to the outer barrel 62 against the bias applied by the spring 86.

The outwardly extended portion of the inner barrel 83 is coupled axially to a transition adapter 68. The transition adapter 68 has a first cylindrical portion that matches the diameter of the inner barrel 83, a second cylindrical portion 72 that has a very small diameter approximating a diameter of a syringe needle, and a conical portion disposed between the first and second cylindrical portions to taper between the two diameters. The transition adapter 68 further has a central bore that extends the axial length of the transition adapter from a first opening at the distal end of the small-diameter cylindrical portion 72 to a second opening at the proximal end of the transition adapter 68 within the inner barrel 83. An interior surface 77 of the transition adapter 68 abuts against a distal end of the tie rod 94 when the inner barrel 83 is biased to the position relative to the outer barrel 62 such that the limit pin 93 is held against the distal end of the axial slots 95, 97.

Figure 12:
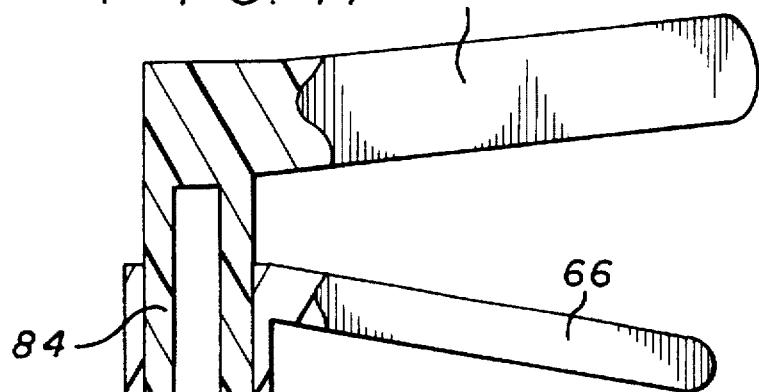
FIG. 12 is an enlarged side view of the alternative surgical apparatus of FIG. 11 illustrating the vein gripping jaws extended to an open position.
Figure 13:
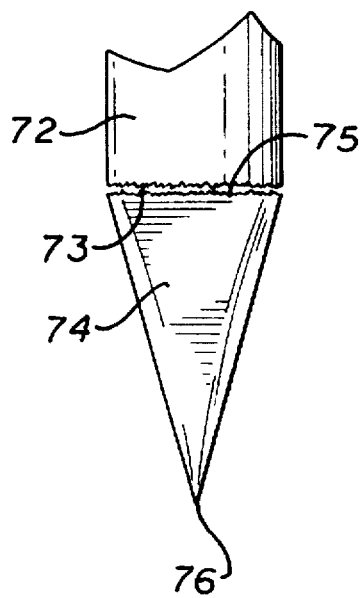
FIG. 13 is an enlarged side view of the alternative surgical apparatus of FIG. 11 illustrating the vein gripping jaws compressed to a closed position.

The tie rod 94 has an axially coupled shaft 82 that extends from the distal end of the tie rod and entirely through the bore in the transition adapter 68. The shaft 82 is movable in an axial direction through the bore in cooperation with movement of the inner barrel 83. A needle 74 is coupled to a distal end of the shaft 82, and has a sharp endpoint 76. The needle 74 has a maximum diameter that is substantially identical to the diameter of the cylindrical portion 72. With the inner barrel 83 biased to the position relative to the outer barrel 62 such that the limit pin 93 is held against the distal end of the axial slots 95, 97, a gap is defined between the arrowhead 74 and the distal end of the cylindrical portion 72, as illustrated at FIG. 12. Conversely, with the inner barrel 83 biased to the position relative to the outer barrel 62 such that the limit pin 93 is held against the proximal end of the axial slots 95, 97, the needle 74 and the distal end of the cylindrical portion 72 compress together, as illustrated at FIG. 13. The needle 74 has a surface 75 that faces a corresponding surface 73 of the cylindrical portion 72, with these surfaces coming into contact as the inner barrel 83 is moved against the bias of the spring 86, similar to the jaws of a forceps. The surfaces 73, 75 may each be provided with a roughened texture in order to improve the gripping ability of the apparatus 60. The needle 74 and the cylindrical portion 72 of the transition adapter 68 may be comprised of a high strength material, such as surgical steel. The maximum diameter of the needle 74 and cylindrical portion 72 may be approximately four millimeters, and in a preferred embodiment of the invention, the surgical apparatus may utilize several incremental diameter sizes, including one, two, three and four millimeter sizes.

Figure 8:
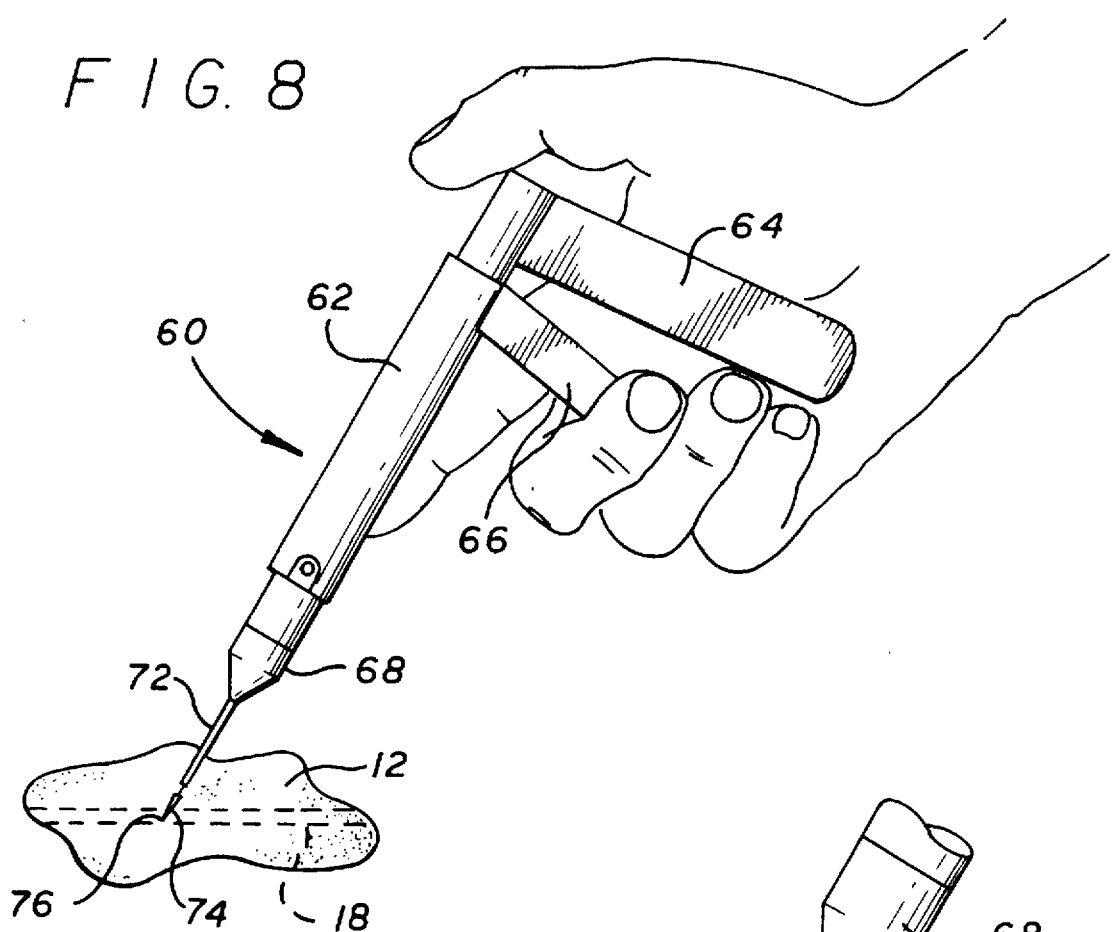
FIG. 8 is a perspective view of a surgeon using an alternative embodiment of the surgical apparatus.
Figure 9:
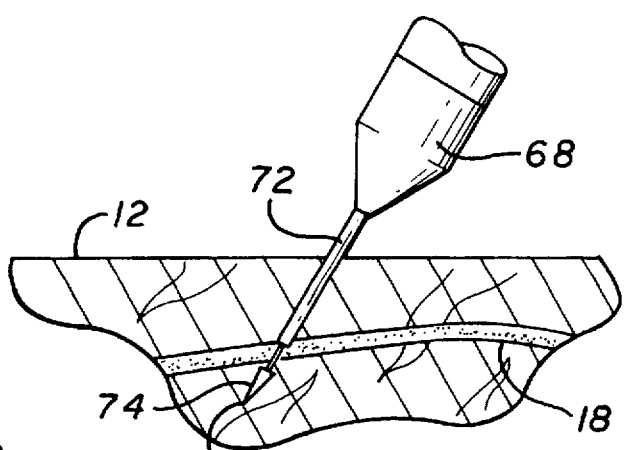
FIG. 9 is a partial perspective view of the alternative surgical apparatus in engagement with an exemplary vein.
Figure 10:
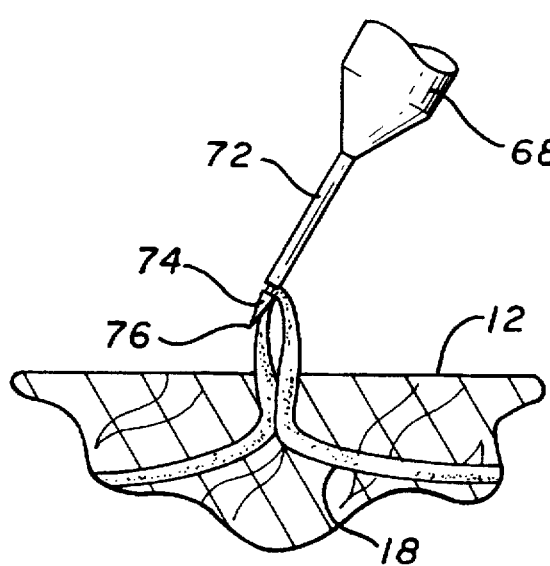
FIG. 10 is a partial perspective view of the alternative surgical apparatus extracting a portion of the exemplary vein.
Figure 11:
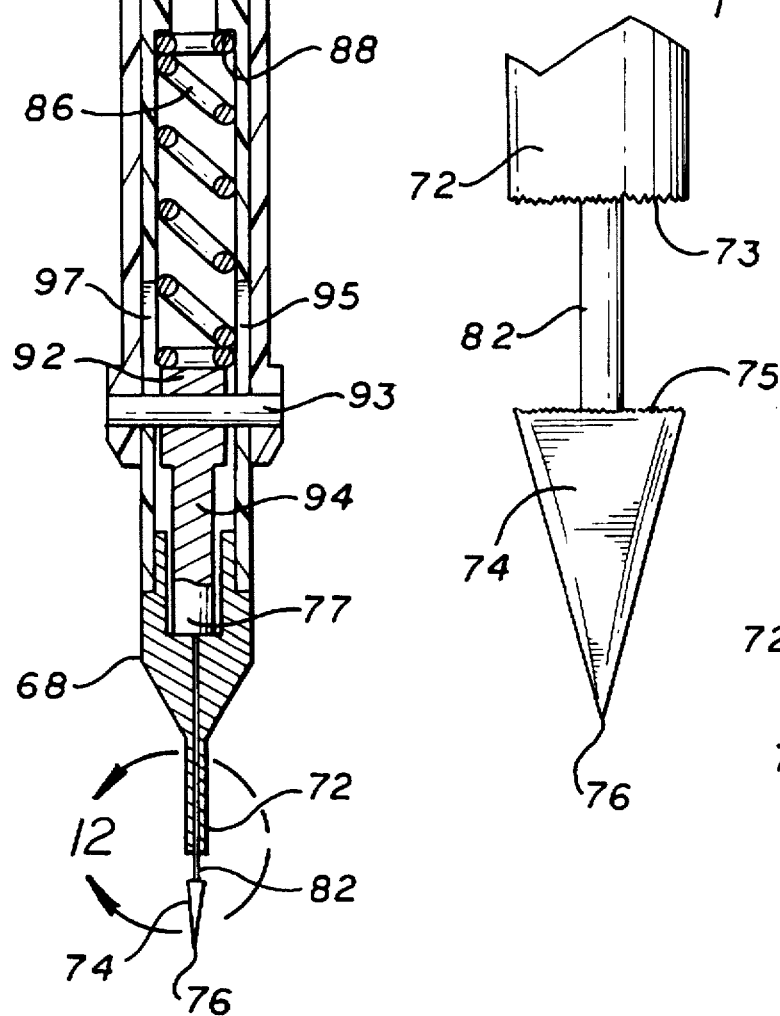
FIG. 11 is a side sectional view of the alternative surgical apparatus.

The use of the surgical apparatus 60 in performing a varicose vein surgical procedure is now described with reference to FIGS. 8 through 10. As described above, a varicose vein segment is traced with a marker on the skin surface while the patient is standing in an upright position prior to conducting the vein surgery. After selecting an appropriate segment of the varicose vein for removal and ligation, the surgical apparatus 60 is used to form an incision through the skin layer at the marked locations. Particularly, the incision may be formed by pushing the needle 74 and cylindrical portion 72 directly into the skin layer 12, which cuts easily due to the extreme sharpness of the endpoint 76 similar to that of a syringe. The needle 74 is extended downward into the skin layer 12 until the gap defined between the needle and the cylindrical portion 72 is adjacent to the vein 18, as shown in FIG. 9. Then, by compressing the handle 64 against the trigger 66, the respective surfaces 73, 75 of the cylindrical portion 72 and the needle 74 come together to grip the vein 18 in a forcepslike manner.

Thereafter, the needle 74 and cylindrical portion 72 are withdrawn from the skin layer 12 along the same axial direction that it was inserted while maintaining the compressing pressure between the handle 64 and the trigger 66. In so doing, the vein 18 which is gripped between the surfaces 73, 75 will be withdrawn along with the needle 74. By continuing to withdraw the needle 74, the vein 18 will eventually be pulled outwardly through the incision formed through the skin layer 12, as shown in FIG. 10. Once the vein 18 is exposed, the surgeon may remove the varicose vein segment and ligate the exposed ends of the vein following removal. Thereafter, the ligated portion of the vein 18 will return back through the incision due in part to the elastic nature of the vein. The incision may then be closed using conventional techniques, such as by using tape strips. As with the first embodiment discussed above, the single surgical instrument that can both form the incision and grip the vein permits the vein surgeon to perform the entire surgical procedure in a single fluid motion.

Having thus described a preferred embodiment of a method for treating varicose veins, it should be apparent to those skilled in the art that certain advantages of the above described system have been achieved. It should also be appreciated that various modifications, adaptations, and alternative embodiments thereof may be made within the scope and spirit of the present invention. The invention is further defined by the following claims.

What is claimed is:

1. A method for treating varicose veins, comprising:
   forming an incision through a skin layer adjacent to a varicose vein using a first portion of a single surgical device;
   engaging said varicose vein using a second portion of said single surgical device to permit removal of a selected portion thereof through said incision; and
   ligating said selected portion of said varicose vein subsequent to removal through said incision, wherein said steps of forming an incision and engaging said varicose vein are performed without switching to another surgical device.

2. The method of claim 1, wherein said first portion of said surgical device further comprises a scalpel edge having a sharpened tip, and said incision forming step further comprises pushing said tip of said scalpel edge through said skin layer.

3. The method of claim 2, wherein said second portion of said surgical device further comprises a hook provided at a portion of said scalpel edge proximal from said tip, and said engaging step further comprises engaging said varicose vein with said hook.

4. The method of claim 1, wherein said first portion of said surgical device further comprises a needle extending from an end of an elongated shaft and having a sharpened tip, and said incision forming step further comprises pushing said sharpened tip through said skin layer.

5. The method of claim 4, wherein said second portion of said surgical device further comprises a cylindrical sleeve concentrically disposed around said shaft and being adapted to move in sliding engagement with said shaft along an axial extent thereof, said needle and said cylindrical sleeve further having respective facing surfaces defining a gripping region therebetween, and said engaging step further comprises moving said cylindrical sleeve relative to said shaft to vary a distance between said respective facing surfaces.

6. The method of claim 1, wherein said first portion of said surgical device and said second portion of said surgical device share a common handle.

7. A method for treating varicose veins, comprising:
   forming an incision through a skin layer adjacent to a varicose vein using a first portion of a single surgical device;
   engaging said varicose vein using a second portion of said single surgical device;
   withdrawing a selected portion of said varicose vein through said incision by withdrawing said single surgical device therethrough; and
   wherein each of said steps are performed without switching to another surgical device.

8. The method of claim 7, wherein said first portion of said surgical device further comprises a scalpel edge having a sharpened tip, and said incision forming step further comprises pushing said tip of said scalpel edge through said skin layer.

9. The method of claim 8, wherein said second portion of said surgical device further comprises a hook provided at a portion of said scalpel edge proximal from said tip, and said engaging step further comprises engaging said varicose vein with said hook.

10. The method of claim 7, wherein said first portion of said surgical device further comprises a needle extending from an end of an elongated shaft and having a sharpened tip, and said incision forming step further comprises pushing said sharpened tip through said skin layer.

11. The method of claim 10, wherein said second portion of said surgical device further comprises a cylindrical sleeve concentrically disposed around said shaft and being adapted to move in sliding engagement with said shaft along an axial extent thereof, said needle and said cylindrical sleeve further having respective facing surfaces defining a gripping region therebetween, and said engaging step further comprises moving said cylindrical sleeve relative to said shaft to vary a distance between said respective facing surfaces.

12. The method of claim 7, wherein said first portion of said surgical device and said second portion of said surgical device share a common handle.

\* \* \* \* \*